US00PP35642P2

(12) United States Plant Patent
Peeters

(10) Patent No.: US PP35,642 P2
(45) Date of Patent: Feb. 6, 2024

(54) ***ZAMIOCULCAS* PLANT NAMED 'ZAM202201'**

(50) Latin Name: *Zamioculcas zamiifolia*
Varietal Denomination: ZAM202201

(71) Applicant: A.C.J. PEETERS HOLDING B.V., Breda (NL)

(72) Inventor: Arjan Peeters, Breda (NL)

(73) Assignee: A.C.J. PEETERS HOLDING B.V., Breda (NL)

( * ) Notice: Subject to any disclaimer, the term of this patent is extended or adjusted under 35 U.S.C. 154(b) by 0 days.

(21) Appl. No.: 18/211,206

(22) Filed: Jun. 16, 2023

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 6/00; A01H 5/12
See application file for complete search history.

*Primary Examiner* — Keith O. Robinson
(74) *Attorney, Agent, or Firm* — C. A. Whealy

(57) ABSTRACT

A new and distinct cultivar of *Zamioculcas* plant named 'ZAM202201', characterized by its compact and upright plant habit with upwardly pointing pinnately-compound leaves; basally clumping habit; vigorous growth habit and moderate growth rate; and glossy leaflets that broadly elliptic and rounded in shape and dark green in color.

2 Drawing Sheets

Figure 1:
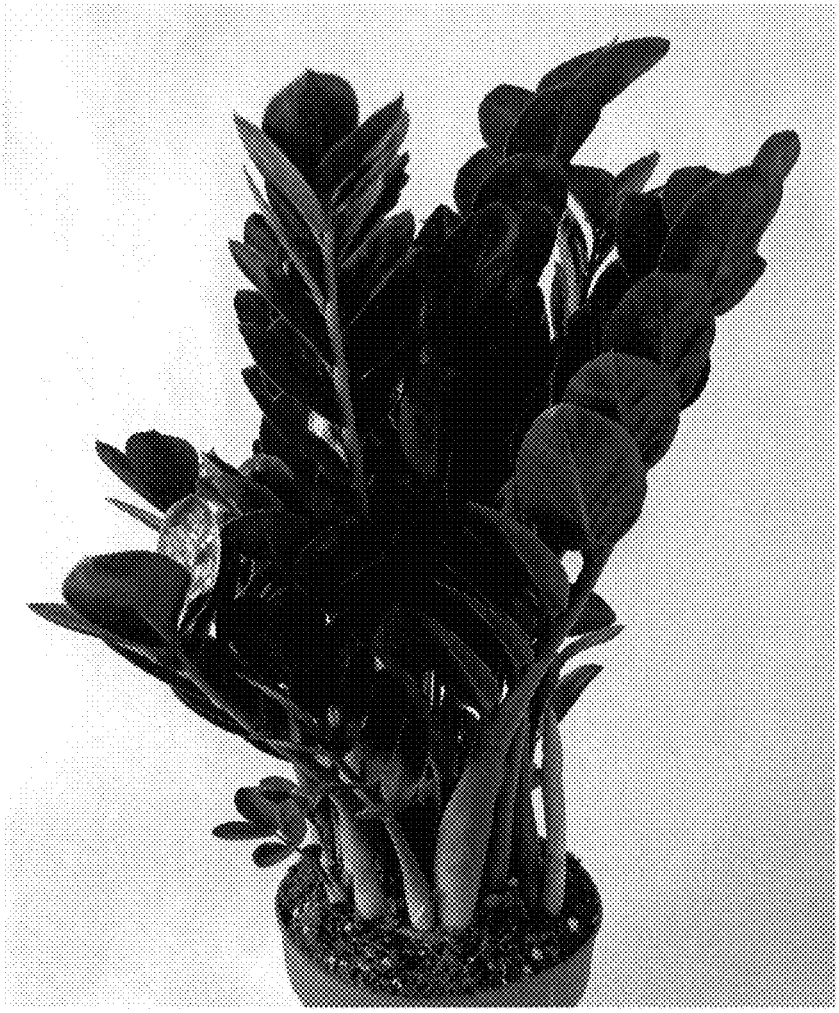

Botanical designation: *Zamioculcas zamiifolia.*
Cultivar denomination: 'ZAM202201'.

PRIOR DISCLOSURES BY INVENTOR & APPLICANT/ASSIGNEE

An European Community Plant Breeder's Rights application for the instant plant was filed by the Applicant/Assignee, A.C.J. Peeters Holding B.V. of Breda, The Netherlands on Dec. 14, 2022, application number 2022/2941. Foreign priority is not claimed to this application.

BACKGROUND OF THE INVENTION

The present invention relates to a new and distinct cultivar of *Zamioculcas* plant, botanically known as *Zamioculcas zamiifolia* and hereinafter referred to by the name 'ZAM202201'.

The new *Zamioculcas* plant is a naturally-occurring whole plant mutation of an unnamed selection of *Zamioculcas zamiifolia*, not patented. The new *Zamioculcas* plant was discovered and selected by the Inventor as a single plant from within a population of plants of the unnamed selection in a controlled greenhouse environment in Breda, The Netherlands in February, 2020.

Asexual reproduction of the new *Zamioculcas* plant by vegetative cuttings in a controlled environment in Breda, The Netherlands since March, 2020 has shown that the unique features of this new *Zamioculcas* plant are stable and reproduced true to type in successive generations of asexual reproduction.

SUMMARY OF THE INVENTION

Plants of the new *Zamioculcas* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ZAM202201'. These characteristics in combination distinguish 'ZAM202201' as a new and distinct *Zamioculcas* plant:

1. Compact and upright plant habit with upwardly pointing pinnately-compound leaves.
2. Basally clumping habit.
3. Vigorous growth habit and moderate growth rate.
4. Glossy leaflets that broadly elliptic and rounded in shape and dark green in color.

Plants of the new *Zamioculcas* differ primarily from plants of the unnamed parent selection in leaflet size, shape and arrangement as plants of the new *Zamioculcas* have smaller, more rounded and more closely-spaced leaflets than leaflets of plants of the unnamed parent selection.

Plants of the new *Zamioculcas* can also be compared to plants of *Zamioculcas zamiifolia* 'Lucky', disclosed in U.S. Plant Pat. No. 23,594. In side-by-side comparisons, plants of the new *Zamioculcas* differ from plants of 'Lucky' in the following characteristics:

1. Plants of the new *Zamioculcas* are more compact than plants of 'Lucky'.
2. Plants of the new *Zamioculcas* are more freely clumping than plants of 'Lucky'.
3. Leaflets of plants of the new *Zamioculcas* are more rounded in shape, more closely-spaced and darker green in color than leaflets of plants of 'Lucky'.

BRIEF DESCRIPTION OF THE PHOTOGRAPHS

The accompanying photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas* plant.

The photograph on the first sheet (FIG. 1) is a side perspective view of a typical plant of 'ZAM202201' grown in a container.

Figure 2:
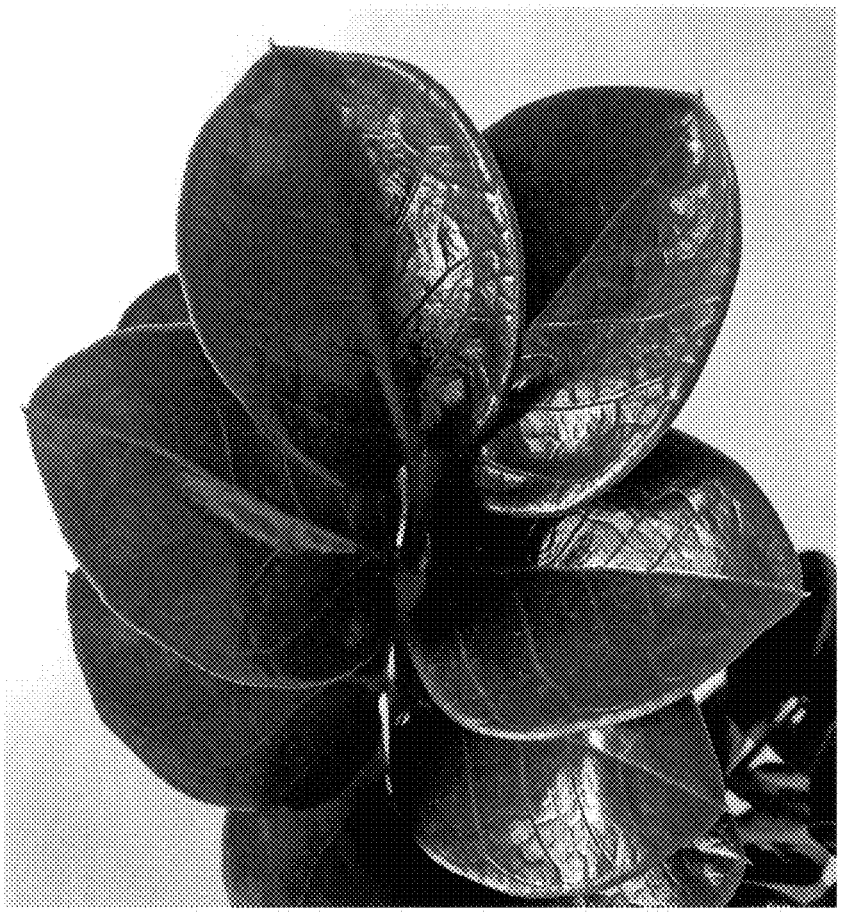

The photograph on the second sheet (FIG. 2) is a close-up view of typical leaflets of a plant of 'ZAM202201'.

DETAILED BOTANICAL DESCRIPTION

The aforementioned photographs and following observations and measurements describe plants grown during the winter and spring in 19-cm containers in a glass-covered greenhouse in Breda, The Netherlands and under cultural practices typical of commercial *Zamioculcas* production. During the production of the plants, day temperatures ranged from 21C to 23C and night temperatures ranged from 19C to 20C. Plants were 18 months old when the photographs and the detailed description were taken. In the following description, color references are made to The Royal Horticultural Society Colour Chart, 2015 Edition, except where general terms of ordinary dictionary significance are used.

Botanical classification: *Zamioculcas zamiifolia* 'ZAM202201'.

Parentage: Naturally-occurring whole plant mutation of an unnamed selection of *Zamioculcas zamiifolia*, not patented.

Propagation:

*Type.*—By vegetative cuttings.

*Time to initiate roots, summer.*—About 56 days at temperatures about 21C.

*Time to initiate roots, winter.*—About 84 days at temperatures about 19C.

*Time to produce a rooted young plant, summer.*—About 84 days at temperatures about 21C.

*Time to produce a rooted young plant, winter.*—About 140 days at temperatures about 19C.

*Root description.*—Medium in thickness, fleshy; brownish white in color; actual color of the roots is dependent on substrate composition, water quality, fertilizer, substrate temperature and age of roots.

*Rooting habit.*—Moderately freely branching, dense.

Plant description:

*Plant and growth habit.*—Compact and upright plant habit with upwardly pointing leaves; overall shape, narrow inverted triangle; stemless; pinnately compound leaves developing in basal clumps; typically about 15 to 20 clumps developing per plant; vigorous growth habit and moderate growth rate.

*Plant height.*—About 50 cm.

*Plant diameter.*—About 40 cm to 45 cm.

Leaf description:

*Leaf arrangement.*—Pinnately compound leaves with about 14 to 16 leaflets per leaf.

*Leaf length.*—About 40 cm to 45 cm.

*Leaflet length.*—About 6 cm to 8 cm.

*Leaflet width.*—About 4 cm.

*Leaflet shape.*—Broadly elliptic and rounded.

*Leaflet apex.*—Obtuse with mucronate tip.

*Leaflet base.*—Obtuse.

*Leaflet margin.*—Entire.

*Leaflet venation.*—Pinnate.

*Leaflet texture and luster, upper and lower surfaces.*—Smooth, glabrous; glossy.

*Leaflet color.*—Developing leaflets, upper surface: Close to 146A. Developing leaflets, lower surface: Close to 146B. Fully expanded leaflets, upper surface: Close to 147A; venation, close to 144B. Fully expanded leaflets, lower surface: Close to 144A; venation, close to 144B.

*Petioles* (*rachis*).—Length: About 10 cm to 15 cm. Diameter: Proximally, about 2 cm; distally, about 1 cm. Texture: Smooth, glabrous. Color: Close to 147B.

Inflorescence description: To date, flower initiation and development has not been observed on plants of the new *Zamioculcas*.

Pathogen & pest resistance: To date, plants of the new *Zamioculcas* have not been observed to be resistant to pathogens or pests common to *Zamioculcas* plants.

Temperature tolerance: Plants of the new *Zamioculcas* have been observed to be tolerant to temperatures ranging from about 10C to about 40C.

It is claimed:

1. A new and distinct *Zamioculcas* plant named 'ZAM202201' as illustrated and described.

* * * * *